United States Patent
Pohl et al.

(10) Patent No.: US 7,495,136 B2
(45) Date of Patent: Feb. 24, 2009

(54) PROCESS FOR THE PRODUCTION OF DINITROTOLUENE

(75) Inventors: Fritz Pohl, Brunsbüttel (DE); Wolfgang Lorenz, Dormagen (DE); Juergen Muennig, Shanghai (CN); Bernd Pennemann, Bergisch Gladbach (DE); Gerhard Wiechers, Leverkusen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/827,502

(22) Filed: Jul. 12, 2007

(65) Prior Publication Data

US 2008/0086017 A1    Apr. 10, 2008

(30) Foreign Application Priority Data

Jul. 21, 2006    (DE)    ........................ 10 2006 033 722

(51) Int. Cl.
    *C07C 205/00*    (2006.01)
(52) U.S. Cl. ....................................................... 568/934
(58) Field of Classification Search ................... 568/934
    See application file for complete search history.

(56) References Cited

U.S. PATENT DOCUMENTS

| | | | | | |
|---|---|---|---|---|---|
| 2,362,743 | A * | 11/1944 | De C Crater | ................. | 568/934 |
| 2,475,095 | A | 7/1949 | Hoek | ........................ | 260/645 |
| 2,947,791 | A | 8/1960 | Adams | ...................... | 260/645 |
| 3,157,706 | A | 11/1964 | Ozeki et al. | .................. | 260/645 |
| 3,708,546 | A * | 1/1973 | Coon et al. | .................. | 568/934 |
| 3,981,933 | A * | 9/1976 | Cook et al. | ................. | 568/934 |
| 4,112,006 | A * | 9/1978 | Schubert et al. | ............. | 568/940 |
| 4,367,347 | A * | 1/1983 | Sawicki | ....................... | 568/934 |
| 4,496,782 | A | 1/1985 | Carr | ........................... | 568/934 |
| 4,642,396 | A * | 2/1987 | Carr et al. | .................... | 568/934 |
| 4,663,490 | A * | 5/1987 | Gerken et al. | ................. | 568/934 |
| 4,918,250 | A * | 4/1990 | Mason et al. | ................ | 568/934 |
| 5,001,286 | A | 3/1991 | Witt et al. | .................... | 568/934 |
| 5,275,701 | A | 1/1994 | Mazzafro et al. | .............. | 203/12 |
| 5,345,012 | A | 9/1994 | Schieb et al. | ................ | 568/934 |
| 5,354,924 | A * | 10/1994 | Mason | ........................ | 568/934 |
| 5,616,818 | A * | 4/1997 | Pirkl et al. | ................... | 568/932 |
| 5,679,873 | A * | 10/1997 | Klingler et al. | ............. | 568/934 |
| 5,689,018 | A * | 11/1997 | Klingler et al. | ............. | 568/934 |
| 5,756,867 | A | 5/1998 | Hermann et al. | ............ | 568/934 |
| 5,902,910 | A * | 5/1999 | Mazzafro et al. | ............ | 568/934 |
| 5,948,944 | A * | 9/1999 | Zhang et al. | ................. | 568/934 |
| 6,258,986 | B1 * | 7/2001 | Klingler et al. | ............. | 568/934 |
| 6,528,690 | B2 * | 3/2003 | Klingler et al. | ............. | 568/934 |
| 6,936,741 | B2 * | 8/2005 | Munnig et al. | ............. | 568/934 |
| 6,984,762 | B2 * | 1/2006 | Dieterich et al. | ............ | 568/934 |
| 7,041,858 | B1 * | 5/2006 | Muennig et al. | ............ | 568/927 |

FOREIGN PATENT DOCUMENTS

| | | |
|---|---|---|
| DE | 10 2004 005 913 A1 | 8/2005 |
| WO | 2005/075407 A1 | 8/2005 |
| WO | WO 2005075407 A1 * | 8/2005 |

* cited by examiner

*Primary Examiner*—Jafar Parsa
(74) *Attorney, Agent, or Firm*—Lyndanne M. Whalen

(57) ABSTRACT

Dinitrotoluene is produced by nitration of toluene with nitrating acid (mixture of nitric acid and sulfuric acid) in which, in a first stage, the toluene is converted to mononitrotoluene (MNT) and then the mononitrotoluene is converted in a second stage to dinitrotoluene (DNT). Control of the weight ratio of the aqueous to organic phases, dispersion of the organic phase in the aqueous phase and use of less than 2.06 moles of nitric acid per mole of toluene are key features of this process.

12 Claims, No Drawings

PROCESS FOR THE PRODUCTION OF DINITROTOLUENE

BACKGROUND OF THE INVENTION

The invention relates to a process for the production of dinitrotoluene by nitration of toluene with nitrating acid (mixture of nitric acid and sulfuric acid) in which, in a first stage, the toluene is converted to mononitrotoluene (MNT) and then the mononitrotoluene is converted in a second stage to dinitrotoluene (DNT).

Dinitrotoluene (DNT) is an intermediate for the production of toluene diisocyanate (TDI), which is an important starting material produced on an industrial scale for the production of polyurethanes.

The production of dinitrotoluene by nitration of toluene with nitrating acid (mixture of nitric acid and sulfuric acid) is known and has been described many times (See, e.g., Ullmann's Enzyklopedie der technischen Chemie, $4^{th}$ edition, volume 17, pages 391 ff, 1979, Verlag Chemie Weinheim/New York). The industrial production takes place, as described, e.g., in H. Hermann, J. Gebauer, P. Konieczny, "Industrial Nitration of Toluene to Dinitrotoluene" in ACS-Symposium, Series 623, 234-249, 1996, ed. L. F. Albright, R. V. C. Carr, R. J. Schmitt, predominantly isothermally with nitric acid in the presence of sulfuric acid as catalyst continuously in two stages, such that a) the reaction mixture obtained in the dinitration (nitration of MNT to DNT) is separated by phase separation and the used acid is fortified again with nitric acid and then mixed with toluene and fed into the mononitration (nitration of toluene to MNT), and b) the reaction mixture from the mononitration is separated in a separating stage on completion of the reaction into an organic phase containing the mononitrotoluene and an aqueous phase predominantly containing the sulfuric acid ("spent acid"), and c) the organic phase containing the mononitrotoluene obtained in b) is fed into the dinitration and the mononitrotoluene is reacted there with nitric acid in the presence of sulfuric acid to form dinitrotoluene.

To achieve commercial specifications, the crude DNT thus obtained is generally treated in downstream stages, predominantly washes, and thus largely freed of dissolved sulfuric and nitric acid contents as well as of secondary components formed in the reaction stages, e.g., cresols and their degradation products. Typical commercial DNT products have DNT contents of >98.5 wt. %, less than 0.1 wt. % mononitrotoluene, less than 0.1 wt. % trinitrotoluene and less than 0.1 wt. % of other secondary components, based on the weight of the DNT product mixture, with DNT yields of >98% and toluene conversions of >99.9%. The weight ratio of the 2,4- and 2,6-DNT isomers in total to the 2,3-, 3,4-, 2,5- and 3,5-DNT isomers in total is also essential. According to commercial specifications, the content of the 2,4- and 2,6-DNT isomers in total in the crude DNT is >95 wt. %, based on the weight of the crude DNT. The content of 2,4-DNT is preferably 79.0-81.0 wt. %, based on the sum of the weights of 2,4-DNT and 2,6-DNT. Accordingly, the content of 2,6-DNT is 19.0-21.0 wt. %, based on the sum of the weights of 2,4-DNT and 2,6-DNT.

In addition to the crude DNT, spent acid is obtained in the separation of the reaction mixture obtained in the mononitration, which leaves the system as a second mass flow. The spent acid generally has a sulfuric acid content of 70-74 wt. % and generally contains >0.1, preferably >0.2 to 1.5 wt. % of unreacted nitric acid, nitrosulfonic acid from oxidation processes occurring in secondary reactions, >0.2 wt. % of MNT, which was not separated off in the phase separation, and generally water in a concentration range of >26 to <30 wt. % (comprising the water introduced with the fresh sulfuric acid fed into the process, water contained in the nitric acid and water formed during the nitrations of the toluene and mononitrotoluene), based in each case on the weight of the spent acid.

In the two-stage isothermal nitration of toluene to dinitrotoluene with nitric acid in the presence of sulfuric acid, both the use of highly concentrated nitric acid (DE 10 2004 005 913 A) and the use of azeotropic and sub-azeotropic nitric acid (EP 0 903 336 A2) in a concentration range of >57 to 69 wt. % are described. Concentrations of >69 wt. % require increased, cost-intensive technical input, which is substantially caused by overcoming the azeotrope.

The concentration of the sulfuric acid used, which acts as a catalyst and as a water-removing agent, is influenced in industrial DNT plants substantially by the concentration of the nitric acid fed into the process and the reaction conditions in the mononitration stage.

It is known that, under suitable conditions, nitric acid is capable not only of nitrating but also of oxidizing the organic compounds in the isothermal two-stage nitration of toluene to dinitrotoluene with nitric acid in the presence of sulfuric acid. Possible compounds obtained by the oxidation of toluene, MNT or DNT are cresols, phenols and their nitration products. A low concentration of sulfuric acid reinforces the oxidizing tendency of nitric acid, so that the content of organic by-products in the reaction mixture increases as the sulfuric acid concentration decreases. On the other hand, as the sulfuric acid concentration falls, the rate of the nitrating reactions desired in the mononitration decreases. Both phenomena lead in industrial DNT plants to a lower limit for the sulfuric acid concentration at which this process can be operated economically. This limit is generally about 70 wt. % (EP 0 903 336 A2).

This limit value has consequences for the sulfuric acid concentration of the spent acid obtained in the phase separation of the dinitration stage and recycled to the mononitration stage. The concentration of $H_2SO_4$ in the spent acid from the dinitration stage is generally greater than 80 wt. %, on the one hand to limit the sulfuric acid throughputs through the mononitration and on the other hand to guarantee a high reaction rate for the nitration in the dinitration stage. Because the concentration of sulfuric acid also has a strong influence on the rate of the desired reactions in the dinitration stage, falling concentrations lead to lower reaction rates.

To meet the concentration requirements outlined and the specifications of an industrial DNT mentioned above, sulfuric acids with concentrations of from 93 to 98 wt. % $H_2SO_4$ or higher, based on the weight of the sulfuric acid, are generally used in industrial DNT plants using the isothermal two-stage process. When sub-azeotropic nitric acids in the range of 60-65 wt. % $HNO_3$, based on the weight of the nitric acid, are used, sulfuric acids with concentrations of more than 95 wt. % $H_2SO_4$, based on the weight of the sulfuric acid, are generally employed. Deviating from this, EP 0 903 336 A2 teaches the use of 86-91 wt. %, preferably 87-89 wt. %, sulfuric acid. The acids used can either be freshly produced or obtained by concentrating the spent acid from the phase separation of the reaction mixture from the mononitration in a concentrating plant.

In addition to this standard process for the 2-stage continuous isothermal nitration of toluene with nitric acid in the presence of sulfuric acid, it has also been proposed to carry out the nitration of toluene to dinitrotoluene with nitrating acid continuously in three stages (EP 903 336 A) or adiabatically in one or two stages in such a way that, as described in EP 597 361 A and EP 696 570 A, all of the heat of reaction from the nitration of the toluene to DNT or only from the DNT stage, as described in EP 696 571, is used to separate off the water of reaction from the nitration and the water introduced into the spent acid by the nitric acid. In addition, it was proposed in U.S. Pat. Nos. 5,948,944 A and 2,362,743 A to carry out the nitration of toluene to DNT only in nitric acid as the reaction medium, thus avoiding the use of sulfuric acid.

In all processes for the production of DNT by nitration of toluene with nitric acid, it is a prerequisite for an economic operating of the process that the spent acids forming in the processes can be reprocessed in such a way that they can be fed into the reaction process again as a reaction medium, as described, e.g., in EP 155 586 A and U.S. Pat. No. 5,275,701 A.

Essential considerations for the selection of a nitrating process, however, are also its inherent process safety, the robustness with which it can be operated, the selectivity and completeness with which the toluene can be converted to dinitrotoluene, and the specific use of nitric acid, which is necessary for the conversion of the toluene to dinitrotoluene.

In view of the above criteria, the industrial-scale production of dinitrotoluene from toluene with nitric acid predominantly takes place according to the so-called nitrating acid or mixed acid process, in which the toluene is reacted continuously with nitric acid in the presence of sulfuric acid in two isothermally operated reaction stages to form dinitrotoluene. In this nitrating acid process, a) the reaction mixture obtained in the dinitration (nitration of MNT to DNT) is separated by phase separation and the used acid thus obtained is fortified again with nitric acid and then mixed with toluene and fed into the mononitration (nitration of toluene to MNT), and b) the reaction mixture from the mononitration is separated in a separating stage on completion of the reaction into an organic phase containing the mononitrotoluene and an aqueous phase predominantly containing the sulfuric acid ("spent acid"), and c) the organic phase obtained in b) containing the mononitrotoluene is fed into the dinitration and the mononitrotoluene is reacted there with nitric acid in the presence of sulfuric acid to form dinitrotoluene.

The selectivity of the toluene reaction is substantially influenced by the sulfuric acid concentration in the two reaction stages of the process. As set out above, sulfuric acid concentrations of <70 wt. % $H_2SO_4$, based on the weight of the sulfuric acid, in the mononitration lead to an increased oxidizing tendency of the nitric acid, and as a result of the oxidation of toluene, MNT or DNT, cresols, phenols and their nitro and degradation products are obtained. On the other hand, sulfuric acid concentrations that are too high in the dinitration stage lead to an increased formation of trinitrotoluene because of the nitric acid that is constantly present.

The desired completeness of the reaction in the reaction stages is also influenced, with a given residence time, by the sulfuric acid concentration and the reaction temperature selected. It is additionally dependent on the nitric acid concentration in the sulfuric acid phase. It also depends on the interfaces produced in the reaction stages, since the reaction mixture in both nitration stages tends to decompose into an organic phase containing only traces of acids and a sulfuric acid phase.

A high specific use of nitric acid, based on the components to be nitrated, does promote their reaction but, on the other hand, it leads to marked nitric acid loadings of the spent acid that is obtained in the phase separation of the mononitration stage or the DNT which is removed in the phase separation of the dinitration stage. It also leads to significant quantities of unreacted nitric acid which have to be removed from both mass flows and reprocessed in subsequent stages and can then be fed back into the reaction stages.

There has been no lack of attempts to improve the isothermal two-stage reaction of toluene with nitric acid in the presence of sulfuric acid with respect to its economic efficiency because the production of dinitrotoluene takes place industrially on such a large scale that even small economic improvements in this important industrial process are of great economic interest.

EP 903 336 A teaches the use of preferably 87-89 wt. % sulfuric acid, which is produced by reprocessing the spent acid from the mononitration and can be obtained with significantly lower expenditure as sulfuric acids with contents of >89 wt. %. The lower sulfuric acid concentration is taken into account by the fact that the process is carried out in three nitration stages rather than two. The organic phase containing the dinitrotoluene obtained in the phase separation of the second stage is fed into a third reaction stage, known as the polishing zone, and is reacted in the polishing zone with a mixed acid containing an aliquot proportion of nitric acid and all of the fresh sulfuric acid fed into the process. The basis of this process is that the sulfuric acid fed into the polishing zone is diluted only by the water content of the aliquot nitric acid feed and the water of reaction formed by the residual nitration taking place in the polishing zone. Acid strengths that are even higher than the acid strengths in a standard process are thus achieved in the polishing zone. A disadvantage of this three stage process, besides the additional investments and operating costs of the third stage, is that the polishing zone has only one reactor. For the complete conversion of the MNT, therefore, so much nitric acid has to be added that the spent acid from the third stage subsequently obtained has a nitric acid content of about 0.4 wt. %. Such nitric acid content, in conjunction with the increased sulfuric acid concentration, presents the risk of increased TNT formation (U.S. Pat. No. 3,157,706 A) on the one hand and, according to experience, lead to nitric acid contents in the discharged DNT of significantly >0.4 wt. %, and thus to significant quantities of unreacted nitric acid, on the other hand.

Minimizing nitric acid losses through the DNT discharge is the goal sought in EP 279 312 A2. EP 279 312 A2 teaches a process for the separation of sulfuric acid and nitric acid from the dinitrotoluenes containing sulfuric acid and nitric acid obtained in the dinitration of toluene with mixed acid. In this disclosed process, the dinitrotoluenes obtained after separating off the greater part of sulfuric acid and nitric acid, which still contain up to 6 wt. % sulfuric acid and up to 5 wt. % nitric acid, are mixed with up to 10 wt. % water, based on the quantity of dinitrotoluenes, and the aqueous phase containing sulfuric and nitric acid that then separates out is removed. The DNT wash is performed in one or more stages in this process.

Improved acid recovery compared with EP 279 312 A2 is taught by EP 736 514 A1. EP 736 514 A1 discloses a process for the removal and recovery of nitric acid, sulfuric acid and nitrogen oxides from the crude dinitrotoluenes formed in the nitration of toluene or mononitrotoluenes after removal of the nitrating acid. In this disclosed process, the crude dinitrotoluenes are extracted in counter-current with a dilute aqueous solution of nitric acid, sulfuric acid and nitrous acid in multiple stages, particularly two to four stages, the volume ratio of the dinitrotoluenes to the aqueous solution being 1:3 to 10:1, preferably 1:1 to 4:1 in each case. The aqueous extract is recycled into the nitration directly or after being concentrated.

In all the extraction stages it is useful to work at a temperature above the melting point of the dinitrotoluenes. The density of the aqueous solution should be different from, preferably lower than, that of the dinitrotoluenes in all the stages. The dilute aqueous solution is usefully circulated within each extraction stage. The desired volume ratio of the dinitrotoluenes to the dilute aqueous solution of nitric acid, sulfuric acid and nitrous acid can be adjusted by adding fresh water into the extraction circulation of the dilute solution from the last extraction stage. In particular, the condensate that forms when the aqueous extract is being concentrated is added. The aqueous solution drawn off from the first extraction stage is a nitric acid/sulfuric acid mixture with 25 to 40 wt. % total acid. This is concentrated alone, or preferably with the nitric acid from treatment of the final mononitrotoluene acid, to a total acid content of 65 wt. %, calculated as $HNO_3$.

With a view to minimizing unused nitric acid, the nitric acid content of the spent acid obtained in the phase separation of the mononitration stage is also the subject of numerous investigations.

U.S. Pat. No. 2,947,791 A teaches an improved continuous process for the nitration of toluene in which equimolar quantities of nitric acid (a component of the nitrating acid of nitric and sulfuric acid, containing 50-60 wt. % sulfuric acid, 20-40 wt. % nitric acid and 10-20 wt. % water) and toluene are reacted at 50 to 100° C. in a well agitated system made up of two reactors connected in series in such a way that 0.4 to 0.7 moles of toluene per mole of nitric acid are fed into the first reactor and the remaining quantity of toluene is then added to the reaction mixture leaving the first reactor and reacted in the second reactor.

As a result of the toluene split performed, a toluene conversion of >95% is obtained in the mononitration stage according to the teaching of U.S. Pat. No. 2,947,791 A, with low contents of nitrogen oxides and nitric acid in the aqueous phase. In the following dinitration, a 5-10% molar excess of nitric acid is then always used.

U.S. Pat. No. 2,475,095 A teaches that residual quantities of toluene in the mononitration reaction mixture make the subsequent phase separation of the reaction mixture more difficult. U.S. Pat. No. 2,475,095 A therefore teaches that an excess of nitric acid compared with toluene is already fed into the mononitration. In this case, the spent acid from the mononitration stage is said to have a nitric acid content of 1 wt. %.

U.S. Pat. No. 4,496,782 A is also based on a nitric acid excess in the mononitration and thus a significant content of nitric acid in the spent acid from the mononitration stage. To use these contents, U.S. Pat. No. 4,496,782 A teaches the addition of additional nitric acid to the spent acid from the mononitration to nitric acid contents of >2 wt. %, and then reacting this nitric acid with an aliquot amount of mononitrotoluene in a stirred reactor adiabatically at temperatures of >110° C. in such a way that, in the subsequent phase separation, spent acids with nitric acid contents of <0.25 wt. % are obtained. In addition to increased technical input, this process presents safety risks.

DE 10 2004 005 913 A1 emphasizes the technical input required for the two-stage isothermal reaction of toluene with nitric acid in the presence of sulfuric acid. According to the teachings of DE 10 2004 005 913 A1, it is essential to reduce this technical input compared with the prior art (which, according to DE 10 2004 005 913 A1, is two- to four-stage agitated vessel cascades in each of the mononitration and dinitration stages). DE 10 2004 005 913 A teaches the use of one agitated vessel in the mononitration stage and the use of two agitated vessels connected in cascade in the dinitration stage.

DE 10 2004 005 913 A1 also teaches an incomplete toluene conversion with, at the same time, significant nitric acid contents in the spent acid (0.96 wt. % in the example illustrating the process taught therein) in the mononitration stage and the complete conversion in the dinitration stage, which is achieved by an appropriate excess of nitric acid.

DE 10 2004 005 913 A1 counters the problem of the significant quantities of unreacted nitric acid withdrawn from the system in the spent acid from the mononitration or dinitration with the following note: "To minimize losses of nitric acid, which does not become nitric acid converted into the end product, as described e.g. in EP 0 736 514, the nitric acid from the wash of the crude DNT is recycled into the nitration as weak acid with a total acid content of 23.73 to 40% total acid together with the nitric acid from the waste gas wash and from the stripping of the spent acid, directly or after being concentrated". DE 10 2004 005 913 therefore replaces the lower expenditure in the reaction stages with increased expenditure in the DNT and spent acid workup stages, and also contains the risk of further reactions in the mononitration stage running out of control and an increased trinitrotoluene (TNT) formation in the dinitration stage.

SUMMARY OF THE INVENTION

The object of the present invention is therefore to provide a process for the reaction of toluene with nitric acid to form dinitrotoluene in the presence of sulfuric acid, which permits a high toluene conversion with high selectivity in terms of DNT and high and selective utilization of the nitric acid fed directly into the reaction stages using a simple plant set-up.

This objective is achieved by the two-stage nitration process for the production of dinitrotoluene of the present invention in which: (1) the weight ratio of aqueous to organic phase in the mononitration step is greater than 2 to 1; (2) the organic phase is dispersed in the aqueous acid-containing phase in each of the nitration reactions; and (3) the amount of nitric acid used per mole of toluene is less than 2.06 moles.

DETAILED DESCRIPTION OF THE INVENTION

It is known that, in the desired isothermal nitration of toluene or mononitrotoluene with nitric acid in the presence of sulfuric acid, the nitration of the aromatics substantially takes place in the aqueous phase of the two phases (Ullmann's Enzyklopädie der technischen Chemie, $4^{th}$ edition, volume 17, p. 391, 1979, Verlag Chemie, Weinheim-New York). In order to react together, the toluene in the mononitration and the mononitrotoluene in the dinitration have to diffuse through the interface between the two phases to react in the aqueous phase in the presence of sulfuric acid with the nitric acid present there.

It is also known that, in such cases, as a function of the reaction conditions such as reaction temperature, the concentration of the components to be reacted in the organic phase and the nitric acid concentration and the sulfuric acid concentration in the aqueous phase, the effective rate of the reaction can depend greatly on the size of the constantly renewed interface, and that this can be increased, e.g., by intensive agitation. This has an advantageous effect on the rate of reaction.

Possible dependences of the constantly renewed interface that can be achieved as a function of the type of mixing and the composition of a system consisting of two immiscible fluids are also described in the literature (J. M. Zaldivar et al., Chemical Engineering and Processing 34 (1995)), 529 ff.

Thus, corresponding dependences in the mononitration of toluene with nitric acid in the presence of sulfuric acid, inter alia, are also reported (ibid.).

Surprisingly, it has now been found that the fundamental dependences described for the reaction of toluene can be observed considerably more markedly for the reaction of mononitrotoluene with nitric acid in the presence of sulfuric acid to form dinitrotoluene.

Thus, in both reaction stages of the isothermal nitration (mononitration and dinitration) of toluene to dinitrotoluene with nitric acid in the presence of sulfuric acid, the size of the constantly renewed interface that can be achieved depends not only on the energy of agitation introduced into the reaction systems but also on the weight ratio of the phases present in the reaction systems. It also depends on which phase is dispersed in which phase.

Thus, with weight ratios of the aqueous to the organic phase of >2:1, preferably >3:1, most preferably >3.5:1 in the mononitration stage and >1.5:1, preferably >3:1, most preferably >3.5:1 in the dinitration stage and with the simultaneous presence of a dispersion of the organic phase in the aqueous phase (and not an inverse dispersion or a "drop in drop" emulsion), constantly renewed interfaces can be obtained that are so large that surprisingly, despite the use of <2.06 moles of nitric acid per mole of toluene in the overall process, largely complete conversion of the toluene to mononitrotoluene and of the mononitrotoluene to dinitrotoluene is achieved.

The present invention relates to a process for the production of dinitrotoluene by nitration of toluene with nitrating acid, in which a) toluene is reacted with nitrating acid to form mononitrotoluene, a reaction mixture being obtained which contains mononitrotoluene, and b) the reaction mixture containing mononitrotoluene is separated into an organic phase containing mononitrotoluene and an aqueous phase containing sulfuric acid, and c) the organic phase containing mononitrotoluene is reacted with nitrating acid, a reaction mixture being obtained which contains dinitrotoluene, and d) the reaction mixture containing dinitrotoluene is separated into an organic phase containing dinitrotoluene and an aqueous phase containing sulfuric acid, in which 1) the weight ratio of aqueous to organic phase in the nitration in step a) is >2:1, preferably >3:1, most preferably >3.5:1 and in step c) >1.5:1, preferably >3:1, most preferably >3.5:1, and 2) in steps a) and c), the organic phase is dispersed in the aqueous phase in each case, and 3) overall, less than 2.06 moles of nitric acid are used per mole of toluene.

It is essential in the process of the present invention that in the mononitration stage (step a) the weight ratio of the aqueous to the organic phase be adjusted to values of >2:1, preferably >3:1, most preferably >3.5:1, and in the dinitration stage (step c) to values of >1.5:1, preferably >3:1, most preferably >3.5:1. It is also essential that in both steps a) and c), the organic phase be dispersed as a disperse phase in the aqueous phase (homogeneous phase) in each case and at the same time, overall less than 2.06 moles of nitric acid per mole of toluene are fed into the process (steps a)-d)).

It is of particular importance in the process of the present invention that the reaction mixture present in both reaction steps a) and c) be in the form of a dispersion in which the organic phase is dispersed in the aqueous as a homogeneous phase in each case. The input of mixing or dispersing energy is preferably selected so that the desired dispersions are produced with very large interfaces but formation of stable "drop in drop" emulsions is avoided. The mixing or dispersing energy advantageously to be introduced into the reaction steps can readily be determined in simple tests. Even when adhering to the phase ratios required for the present invention, the amount of energy required depends on the reactor and agitator geometry selected and the physical data of the reaction mixtures. Once adjusted, the state of the dispersions present in the reaction systems can, however, be monitored advantageously via the conductivity of the homogeneously intermixed reaction mixtures.

The nitration reaction in step a) and/or in step c) is preferably carried out isothermally.

In a preferred embodiment of the present invention, the reaction in each of reaction steps a) and c) takes place in cascades of reactors, in which mixing takes place, preferably in cascades with 2 to $\leq 4$ reactors in each case. In a particularly preferred form, loop reactors containing circulation pumps and heat exchangers are used as reactors.

In a more preferred embodiment of the invention, two loop reactors connected in series, containing circulation pumps and heat exchangers, are used in the mononitration stage. In the dinitration stage, two loop reactors connected in series, containing circulation pumps and heat exchangers, are then used and, in addition, another loop reactor containing a circulation pump but no heat exchanger. The dimensions of the circulation pumps are such that dispersion of the organic phase in the homogeneous aqueous phase always takes place. In this embodiment, a conductivity measurement preferably takes place in at least one of the reactors used, for the continuous monitoring of the state of the circulated dispersion.

A phase separation step b) and d) follows the reaction steps a) and c) respectively. Any apparatus suitable for phase separation can be employed. Both dynamic and static separators are suitable. In a preferred embodiment, static separators are employed in both stages (steps b) and d)).

In the process of the present invention, the toluene is fed into the mononitration stage in step a). The feed of the toluene preferably takes place into the first reactor, but it is also possible to split the toluene addition over several reactors. The toluene fed into the first reactor is preferably added to the reactor mixed with the nitrating acid via one or more nozzles. To this end, the aqueous phase containing sulfuric acid from step d) (spent acid from the dinitration stage) is preferably mixed with nitric acid in advance, thus producing the nitrating acid. However, fresh sulfuric acid or a mixture of fresh sulfuric acid and the spent acid from the dinitration stage can also be used.

Separate addition of the toluene and the nitrating acid is also possible. The separate addition of the nitric acid and the sulfuric acid, e.g. the spent acid from the dinitration stage, is also possible. The weight ratio of the phases in the reactors of the mononitration stage is preferably adjusted via the quantity of the sulfuric acid, e.g. the spent acid from the dinitration stage, fed into the reactors. However, it is also possible to recycle the aqueous phase containing sulfuric acid from the mononitration stage obtained in step b), the recycled aqueous phase containing sulfuric acid preferably being fed into the first reactor of the stage. Addition to several reactors of the stage is also possible, however. A split of the nitric acid fed into the mononitration over several reactors is also possible.

In a particularly preferred embodiment of the present invention, $\leq 1.03$ moles of nitric acid per mole of toluene are fed into the mononitration stage (step a)). Overall, <2.06 moles of nitric acid per mole of toluene are used in the process over the two nitration stages.

The reaction of the toluene takes place in the mononitration stage (step a)) in a temperature range of from 30 to 70° C., it being possible to operate the reactors of the mononitration stage at the same reaction temperature. However, different reaction temperatures in the individual reactors, adapted to the progress of the reaction, are also possible.

The dispersions present in the reactors of the mononitration stage (step a)) are preferably monitored continuously with the aid of conductivity measurements. Thus, impermissible deviations, which can be recognized, for example, from a significant reduction in the conductivity of the circulated reaction mixtures, are corrected by changes to the mixing energy input into the reactors via the mixing or dispersing devices or, preferably, by a change in the phase ratio in the reactors of the nitration stage.

In the process of the present invention, a very high toluene conversion is achieved with a very effective utilization of the nitric acid fed into the mononitration stage. The aqueous phase containing sulfuric acid (spent acid) obtained in the subsequent phase separation typically has a nitric acid content of <0.1 wt. %, based on the weight of the spent acid. This low nitric acid content leads to the very low specific nitric acid requirement of the process of the present invention. In addition, it reduces the expenditure needed for concentrating the spent acid from the mononitration stage.

In the process of the present invention, the organic phase obtained in the phase separation from the mononitration stage (step b)) is preferably fed into the reactors of the dinitration stage (step c)) without any further workup. The feed of the organic phase containing MNT preferably takes place into the first reactor, but a split over several reactors is also possible. The MNT fed into the first reactor is preferably added to the reactor mixed with the nitrating acid using one or more nozzles. To this end, the aqueous phase containing sulfuric acid from step b) (spent acid from the mononitration stage) is optionally reprocessed and mixed with nitric acid preferably in advance, thus producing the nitrating acid. However, fresh sulfuric acid or a mixture of fresh sulfuric acid and the spent acid from the mononitration stage can also be used. Separate addition of the MNT-containing organic phase from step b) and the nitrating acid is also possible. The separate addition of the nitric acid and the sulfuric acid, e.g. the reprocessed spent acid from the mononitration stage, is also possible. The weight ratio of the phases in the reactors of the dinitration stage (step c)) is preferably adjusted via the quantity of the sulfuric acid, e.g. the reprocessed spent acid from the mononitration stage, fed into the reactors. However, it is also possible to recycle the aqueous phase containing sulfuric acid from the dinitration stage obtained in step d), the recycled aqueous phase containing sulfuric acid preferably being fed into the first reactor of the stage. Addition to several reactors of the stage is also possible, however. A split of the nitric acid fed into the dinitration over several reactors is also possible.

In a particularly preferred embodiment of the present invention, ≦1.03 moles of nitric acid per mole of mononitrotoluene are fed into the dinitration (step c)). Overall, <2.06 moles of nitric acid per mole of toluene are used in the process over the two nitration stages.

The reaction of the mononitrotoluene takes place in the dinitration stage (step c)) in a temperature range of from 55 to 80° C., it being possible to operate the reactors of the dinitration stage at the same reaction temperature. However, different reaction temperatures in the individual reactors, adapted to the progress of the reaction, are also possible.

The dispersions present in the reactors of the dinitration stage (step c)) are preferably monitored continuously with the aid of conductivity measurements. Thus, impermissible deviations, which can be recognized, for example, from a significant reduction in the conductivity of the circulated reaction mixtures, are corrected by changes to the mixing energy input into the reactors via the mixing or dispersing devices or, preferably, by a change in the phase ratio in the reactors of the nitration stage.

In the process of the present invention, a very high mononitrotoluene conversion is achieved with a very effective utilization of the nitric acid fed into the dinitration stage. The aqueous phase containing sulfuric acid (spent acid) obtained in the subsequent phase separation typically has a nitric acid content of <0.2 wt. %, based on the weight of the spent acid. The loading of the DNT-containing organic phase obtained in step d) with nitric acid are <0.4 wt. % $HNO_3$, based on the weight of the organic phase.

Overall, the process of the present invention produces DNT in yields of >97.7%, based on the nitric acid used. Such high DNT yields based on the nitric acid used can be achieved with the prior art processes only by expensive treatments of the spent acid obtained in the mononitration or of aqueous phases obtained in downstream extractions and/or washes.

Thus, the process of the present invention is distinguished from the prior art processes by a very high DNT yield based on the nitric acid used, with, at the same time, a simple plant set-up. The low nitric acid requirement of the present invention is achieved without any of the expensive and energy-intensive additional nitric acid recoveries used in the prior art processes to achieve low specific nitric acid consumptions.

It is essential for the low specific nitric acid consumptions without the reprocessing of any spent acids and washing waters that the organic phase be dispersed in the aqueous phase in both reaction stages. This is made possible or made much easier by pre-setting certain weight ratios of the phases in the reaction steps a) and c). As a result, with suitably selected reactor configurations, it is possible to obtain greatly enlarged, rapidly renewed interfaces between organic and aqueous phases compared with an inverted dispersion with the same energy input. The surprisingly high DNT yields based on the nitric acid used, with approximately the same sulfuric acid concentration and lower nitric acid concentrations in the reaction stages compared with the prior art, thus become possible.

The reaction ratios in the dinitration stage (step c)) are of particular importance in the present invention. As a result of the large, rapidly renewed interfaces that can be achieved in the process of the present invention, the transport limitation of the reaction of the mononitrotoluene is largely eliminated. Thus, with approximately the same sulfuric acid concentration, lower residual concentrations of nitric acid are necessary in the reaction mixture leaving the stage for the complete conversion of the MNT. The lower contents of nitric acid also lead to distinctly lower nitric acid loadings of the organic phase containing dinitrotoluene obtained in the subsequent phase separation (step d)) and thus to a distinct reduction in the unreacted nitric acid withdrawn from the reaction system a)-d).

EXAMPLES

General

The nitrations were carried out in continuously operable, 2-stage laboratory apparatus, composed in each case of
- feed vessels with metering pumps,
- two reactors connected in series (stirred vessels with heating/cooling jackets and high-speed laboratory stirrers),
- a separator installed in the discharge of the second reactor and
- downstream receivers to collect the separated phases, it being possible in each case for the aqueous phase collected to be recycled via an additional metering pump to the first reactor of the respective cascade.

In carrying out the nitrations, sulfuric acid was initially charged into the apparatus, which had been rendered inert, in the concentrations to be expected in continuous operation, and the components were then metered in the weight ratios and masses given below, while adjusting the input of mixing energy into the reactors via the agitators with a view to an optimum value of the conductivities measured in the finely dispersed reaction systems.

After reaching stationary equilibrium, the organic phases discharged from the separators were analyzed with respect to their conversion, and in the case of the DNT phase also with respect to the composition of their main components and their nitric acid loading. The aqueous phases discharged from the separators were also investigated with respect to their nitric acid contents.

In addition, the phases were analyzed qualitatively for by-products. Nitrocresols and nitrobenzoic acids were found to a small extent in different degrees of nitration.

Example 1

Not According to the Invention 720 g per hour of a 96% sulfuric acid were mixed continuously with 331 g of a 98.5% nitric acid (to form nitrating acid), this mixture was metered continuously into the first reactor of the DNT stage with 685.7 g/h of crude MNT from the MNT stage and was reacted there at a temperature of 70° C. and conductivities of approx. 90 mS in the reactor cascade. The fully reacted reaction mixture was separated in the subsequent separator into an organic and an aqueous phase.

The aqueous phase of the dinitration stage was in turn mixed continuously with 331 g per hour of a 98.5% nitric acid, this mixture was metered continuously with 460.7 g/h of toluene into the first reactor of the MNT stage, and was reacted there at a temperature of 50° C. and conductivities of approx. 80 mS in the reactor cascade. The reaction mixture overflowing into the separator was separated there into an organic and an aqueous phase, and the organic phase was then fed continuously into the dinitration stage and the aqueous phase was transferred to a workup.

The results achieved are compiled in Table 2.

Example 2

According to the Invention 715 g per hour of a 96% sulfuric acid were mixed continuously with 328 g of a 98.5% nitric acid (to form nitrating acid), this mixture was metered continuously into the first reactor of the DNT stage with 685.7 g/h of crude MNT from the MNT stage and 2190 g/h of aqueous phase from the separator of the DNT stage and was reacted there at a temperature of 70° C. and conductivities of approx. 160 mS in the reactor cascade. The fully reacted reaction mixture was separated in the subsequent separator into an organic and an aqueous phase.

The aqueous phase of the dinitration stage was in turn mixed continuously with 328 g per hour of a 98.5% nitric acid, this mixture was metered continuously with 460.7 g/h of toluene and 2310 g/h of aqueous phase from the separator of the MNT stage into the first reactor of the MNT stage, and was reacted there at a temperature of 50° C. and conductivities of approx. 120 mS in the reactor cascade. The reaction mixture overflowing into the separator was separated into an organic and an aqueous phase, and the organic phase was then fed continuously into the dinitration stage and the aqueous phase was transferred to a workup.

The results achieved are also compiled in Table 2.

Example 3

According to the Invention 275.4 g per hour of a 92% sulfuric acid were mixed continuously with 474.9 g of a 68% nitric acid (to form nitrating acid), this mixture was metered continuously into the first reactor of the DNT stage with 685.7 g/h of crude MNT from the MNT stage and was reacted there at a temperature of 70° C. and conductivities of approx. 160 mS in the reactor cascade. The fully reacted reaction mixture was separated in the subsequent separator into an organic and an aqueous phase.

The aqueous phase of the dinitration stage was in turn mixed continuously with 474.9 g per hour of a 68% nitric acid, this mixture was metered continuously with 460.7 g/h of toluene into the first reactor of the MNT stage, and was reacted there at a temperature of 50° C. and conductivities of approx. 120 mS in the reactor cascade. The reaction mixture overflowing into the separator was separated there into an organic and an aqueous phase, and the organic phase was then fed continuously into the dinitration stage and the aqueous phase was transferred to a workup.

The results achieved are also compiled in Table 2.

It can be seen from the column "Nitric acid di stage" in Table 2 that the necessary quantity of nitric acid in Examples 2 and 3 according to the invention (in which the weight ratio of aqueous to organic phase in the nitration in step a) is >2:1 and in step c) >1.5:1) was lower than in Example 1, which was not according to the invention. This results from the fact that, under the optimized operating conditions of the process of the present invention, the nitric acid was used almost completely and was thus consumed, which can be seen from the quantity of nitric acid discharged in the column "HNO$_3$ residue in spent acid di" in Table 2.

Similar statements also apply to the mononitration stage, as shown by the data in the columns "Nitric acid mono stage" and "HNO$_3$ residue in spent acid mono".

TABLE 1

| | Acid Concentrations | |
|---|---|---|
| Example No. | Nitric acid concentration [wt. %] | Sulfuric acid concentration [wt. %] |
| 1 | 98.5 | 96 |
| 2 | 98.5 | 96 |
| 3 | 68.0 | 92 |

TABLE 2

| Example No. | Toluene [mol] | Nitric acid mono stage [mol] | HNO₃ residue in spent acid mono [%] | Toluene conversion [mol %] | Temperature mono stage [° C.] | Spent acid mono recycling [g] | Phase ratio mass (inorg.)/ mass (org.) |
|---|---|---|---|---|---|---|---|
| 1 | 5.00 | 5.175 | 0.09 | >99.9 | 50 | 0 | 1.34 |
| 2 | 5.00 | 5.125 | 0.005 | >99.9 | 50 | 2310 | 4.69 |
| 3 | 5.00 | 5.125 | 0.005 | >99.9 | 50 | 0 | 4.72 |

| Example No. | Nitric acid di stage [mol] | Sulfuric acid di stage [g] | HNO₃ residue in spent acid di [%] | MNT conversion [mol %] | TNT content [%] | Temperature di stage [° C.] | Spent acid di recycling [g] | Phase ratio mass (inorg.)/ mass (org.) |
|---|---|---|---|---|---|---|---|---|
| 1 | 5.175 | 720 | 0.43 | >99.9 | <0.05 | 70 | 0 | 0.89 |
| 2 | 5.125 | 715 | 0.13 | >99.9 | <0.05 | 70 | 2190 | 3.30 |
| 3 | 5.125 | 2752 | 0.13 | >99.9 | <0.05 | 70 | 0 | 3.29 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of dinitrotoluene by the nitration of toluene with nitrating acid comprising:
   a) reacting an organic phase comprising toluene with an aqueous phase comprising nitrating acid to form a reaction mixture containing mononitrotoluene,
   b) separating the reaction mixture containing mononitrotoluene into an organic phase containing mononitrotoluene and an aqueous phase containing sulfuric acid,
   c) reacting the organic phase containing mononitrotoluene with nitrating acid to form a reaction mixture containing dinitrotoluene, and
   d) separating the reaction mixture containing dinitrotoluene into an organic phase containing dinitrotoluene and an aqueous phase containing sulfuric acid
   in which
   1) a weight ratio of the aqueous phase to the organic phase in step a) is >2:1,
   2) a weight ratio of the aqueous phase to the organic phase in step c) >1.5:1,
   3) the organic phase is dispersed in the aqueous phase in step a),
   4) the organic phase is dispersed in the aqueous phase in step c), and
   5) less than 2.06 moles of nitric acid are used per mole of toluene.

2. The process of claim 1 in which a portion of the aqueous phase containing sulfuric acid obtained in step d) is recycled to step c) to establish a weight ratio of the aqueous phase containing sulfuric acid to the organic phase containing dinitrotoluene of >1.5 in step d).

3. The process of claim 2 in which at least a portion of the aqueous phase containing sulfuric acid obtained in step d) is recycled to a first reactor in a cascade of up to 4 reactors.

4. The process of claim 1 in which the aqueous phase containing sulfuric acid obtained in step d) is recycled completely or partly to step a).

5. The process of claim 1 in which the aqueous phase containing sulfuric acid obtained in step b) is fed completely or partly to step c).

6. The process of claim 1 in which the reaction in step a) and/or step c) is carried out isothermally.

7. The process of claim 1 in which a static separator is used for the phase separation in step b) and/or step d).

8. The process of claim 1 in which step a) and/or step c) is carried out in a cascade of up to 4 reactors.

9. The process of claim 8 in which the last reactor in step c) is a tube reactor.

10. The process of claim 1 in which step a) and/or step c) takes place in a loop reactor.

11. The process of claim 1 in which ≦1.03 moles of nitric acid are used per mole of toluene in step a).

12. The process of claim 1 in which ≦1.03 moles of nitric acid are used per mole of mononitrotoluene in step c).

* * * * *